United States Patent
Lowet et al.

(10) Patent No.: US 10,896,759 B2
(45) Date of Patent: Jan. 19, 2021

(54) INTELLIGENT GROUPING OF PEERS IN MOTIVATIONAL PROGRAMS

(71) Applicant: KONINKLIJKE PHILIPS N.V., Eindhoven (NL)

(72) Inventors: Dietwig Jos Clement Lowet, Eindhoven (NL); Roger Holmes, Son en Breugel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 164 days.

(21) Appl. No.: 16/323,009

(22) PCT Filed: Aug. 10, 2017

(86) PCT No.: PCT/EP2017/070320
§ 371 (c)(1),
(2) Date: Feb. 4, 2019

(87) PCT Pub. No.: WO2018/029297
PCT Pub. Date: Feb. 15, 2018

(65) Prior Publication Data
US 2019/0189285 A1 Jun. 20, 2019

Related U.S. Application Data

(60) Provisional application No. 62/373,640, filed on Aug. 11, 2016.

(51) Int. Cl.
*G16H 50/30* (2018.01)
*G06Q 50/00* (2012.01)
(Continued)

(52) U.S. Cl.
CPC ............. *G16H 50/30* (2018.01); *G06Q 10/06* (2013.01); *G06Q 10/06393* (2013.01);
(Continued)

(58) Field of Classification Search
CPC ........ G16H 50/30; G16H 20/00; G06Q 50/22; G06Q 10/06; G06Q 10/06393; G06Q 50/01
See application file for complete search history.

(56) References Cited

U.S. PATENT DOCUMENTS 7,552,060 B2   6/2009   Vest
7,720,855 B2   5/2010   Brown
(Continued)

FOREIGN PATENT DOCUMENTS

WO   2015084863 A1   6/2015
WO   2016049090 A2   3/2016

OTHER PUBLICATIONS

Zhang, J. et al., "Efficacy and causal mechanism of an online social media intervention to increase physical activity: Results of a randomized controlled trial", University of Pennsylvania, 2015.
(Continued)

*Primary Examiner* — Linh Giang Le

(57) ABSTRACT

This disclosure describes systems and methods for facilitating social ranking and grouping via received signals conveying health-related information. The system may receive signals conveying health-related information associated with a user; determine health-related information associated with the user based on the received signals; determine one or more motivational criteria for the user; aggregate the user and other users into one or more groups; determine one or more social rankings of the user within the one or more groups based on the health-related information; select a first peer group for the user from the one or more groups based on the one or more social rankings of the user and the one or more motivational criteria for the user; and effectuate presentation of the user's social ranking within the first peer group.

15 Claims, 2 Drawing Sheets

(51) Int. Cl.
*G06Q 50/22* (2018.01)
*G06Q 10/06* (2012.01)
*G16H 20/00* (2018.01)

(52) U.S. Cl.
CPC ............ *G06Q 50/01* (2013.01); *G06Q 50/22* (2013.01); *G16H 20/00* (2018.01)

(56) References Cited

U.S. PATENT DOCUMENTS

| | | |
|---|---|---|
| 2002/0045154 A1 | 4/2002 | Wood et al. |
| 2011/0276396 A1* | 11/2011 | Rathod ................ H04L 51/066 705/14.49 |
| 2015/0025997 A1 | 1/2015 | Chan |

OTHER PUBLICATIONS

"Social comparison theory", Wikipedia, https://en.wikipedia.org/wiki/Social_comparison_theory, Accessed Jan. 2019.
Malhotra, D., "The desire to win: The effects of competitive arousal on motivation and behavior", Harvard Business School, 2009.

\* cited by examiner

INTELLIGENT GROUPING OF PEERS IN MOTIVATIONAL PROGRAMS

CROSS-REFERENCE TO PRIOR APPLICATIONS

This application is the U.S. National Phase application under 35 U.S.C. § 371 of International Application No. PCT/EP2017/070320, filed on 10 Aug. 2017, which claims the benefit of U.S. Provisional Patent Application No. 62/373,640, filed on 11 Aug. 2016. These applications are hereby incorporated by reference herein.

TECHNICAL FIELD

Various embodiments of the present disclosure pertain to wearable devices and coaching programs. More specifically, but not exclusively, various embodiments relate to a system and method for facilitating social ranking and grouping via received signals conveying health-related information.

BACKGROUND

Being part of a social group or peer group may provide an incentive or a motivating force that may help in personal health behavior change programs. A peer group may instill competitive drive, provoke guilt, promote collaboration, lead to receiving motivational messages from peers, or cater for social comparisons that may lead to enforcing positive tendencies, decreasing of negative behavioral tendencies, or normalizing results of past behavior. Existing approaches to peer group selection (e.g., friends on a social network, manual selection by participant, participants with similar baseline statistics) may not reliably pick a peer group that is optimally motivating to a user. Moreover, although existing approaches provide users with rankings within their respective groups to further motivate users, users typically need access to the Internet to obtain ranking updates, thereby limiting a user's motivation influenced by such ranking updates in circumstances where the user has little or no Internet connection.

SUMMARY

Accordingly, one or more aspects of the present disclosure relate to a system configured to facilitate social ranking and grouping via received signals conveying health-related information. The system includes one or more processors or other components. The one or more processors are configured by machine-readable instructions to receive signals conveying health-related information associated with a user; determine health-related information associated with the user based on the received signals; determine one or more motivational criteria for the user; aggregate the user and other users into one or more groups; determine one or more social rankings of the user within the one or more groups based on the health-related information; select a first peer group for the user from the one or more groups based on the one or more social rankings of the user and the one or more motivational criteria for the user; and; effectuate presentation of the user's social ranking within the first peer group.

Another aspect of the present disclosure relates to a method for facilitating social ranking and grouping via received signals conveying health-related information with a system and to a non-transitory machine readable medium encoded with instructions for execution by a processor for performing a method. In various embodiments the method includes one or more processors or other components. The method includes receiving, with the one or more processors, signals conveying health-related information associated with a user; determining, with the one or more processors, health-related information associated with the user based on the received signals; determining, with the one or more processors, one or more motivational criteria for the user; aggregating, with the one or more processors, the user and other users into one or more groups; determining, with the one or more processors, one or more social rankings of the user within the one or more groups based on the health-related information; selecting, with the one or more processors, a first peer group for the user from the one or more groups based on the one or more social rankings of the user and the one or more motivational criteria for the user; and effectuating, with the one or more processors, presentation of the user's social ranking within the first peer group.

Still another aspect of present disclosure relates to a system for facilitating social ranking and grouping via received signals conveying health-related information. The system includes means for receiving signals conveying health-related information associated with a user; means for determining health-related information associated with the user based on the received signals; means for determining one or more motivational criteria for the user; means for aggregating the user and other users into one or more groups; means for determining one or more social rankings of the user within the one or more groups based on the health-related information; means for selecting a first peer group for the user from the one or more groups based on the one or more social rankings of the user and the one or more motivational criteria for the user; and means for effectuating presentation of the user's social ranking within the first peer group.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

Various embodiments are described wherein the one or more motivational criteria are determined based on at least one of a most motivational ranking, a most normalizing ranking, and a most preventative ranking, and wherein the one or more motivational criteria comprise: being affiliated with a lower part of the first peer group, wherein the user is motivated by social upward comparison; being affiliated with an upper part of the first peer group, wherein the user is motivated by social downward comparison; being almost highest ranked within the first peer group, wherein the user is motivated by competition; making more progress with respect to the social ranking within the first peer group than an average progress with respect to the social ranking within the first peer group, wherein the user is motivated by social upward comparison; or making less progress with respect to the social ranking within the first peer group than an average progress with respect to the social ranking within the first peer group, wherein the user is motivated by social downward comparison, and wherein the average progress is determined by averaging progress made by the user and each of the other users of the first peer group with respect to the social ranking.

Various embodiments are described wherein the determined health-related information includes at least one of a current health status, an adherence to a program, an amount of physical activity, an amount of weight loss, and a fitness level of the user.

Various embodiments additionally include a user device, the user device including one or more sensors configured to generate signals conveying the health-related information associated with the user, wherein the user device is configured to: receive health-related information associated with the other users of the first peer group over a network in communication with the one or more processors; determine an auxiliary social ranking of the user within the first peer group based on the health-related information associated with the user and the health-related information associated with the other users of the first peer group; determine, based on further signals generated by the one or more sensors, additional health-related information associated with the user; update the auxiliary social ranking of the user based on the additional health-related information such that the user's updated auxiliary social ranking is different than the user's social ranking within the first peer group at a given time; and effectuate presentation of the user's updated auxiliary social ranking at the user device.

Various embodiments are described wherein the one or more processors are further configured to: responsive to the user achieving a social ranking corresponding to the one or more motivational criteria within the first peer group, maintain the user within the first peer group with the social ranking corresponding to the one or more motivational criteria for a predetermined amount of time; and subsequent to maintaining the user within the first peer group with the social ranking corresponding to the one or more motivational criteria for the predetermined amount of time, place the user in a second peer group such that the user has not yet achieved the social ranking corresponding to the one or more motivational criteria within the second peer group, the second peer group having at least one different individual member than the first peer group.

Various embodiments are described wherein the one or more processors are configured to aggregate the user and the other users into the one or more groups based on one or more similarity criteria, wherein the one or more similarity criteria is determined based on information provided on the user's profile and the other users' profiles.

Various embodiments are described wherein the similarity criteria comprises at least one of a gender, a location, an occupation, a marital status, an employment status, an education level, an age, an activity level, a fitness level, and an interest of the user and each of the other users.

DETAILED DESCRIPTION

The description and drawings presented herein illustrate various principles. It will be appreciated that those skilled in the art will be able to devise various arrangements that, although not explicitly described or shown herein, embody these principles and are included within the scope of this disclosure. As used herein, the term, "or," as used herein, refers to a non-exclusive or (i.e., and/or), unless otherwise indicated (e.g., "or else" or "or in the alternative"). Additionally, the various embodiments described herein are not necessarily mutually exclusive and may be combined to produce additional embodiments that incorporate the principles described herein.

Figure 1:
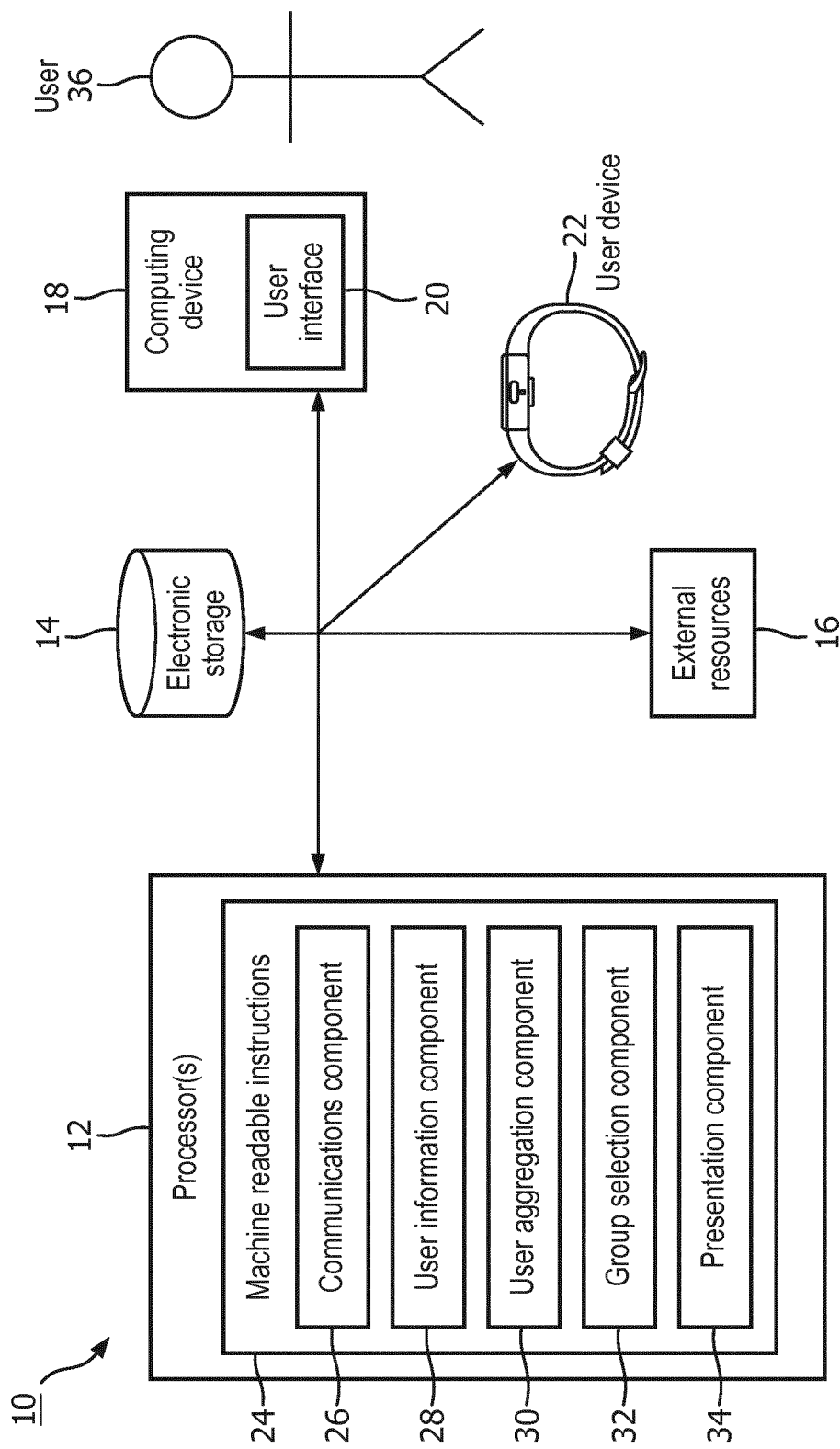
FIG. 1 is a schematic illustration of a system configured to facilitate social ranking and grouping via received signals conveying health-related information according to one or more embodiments.

FIG. 1 is a schematic illustration of a system 10 configured to facilitate social ranking and grouping via received signals conveying health-related information. System 10 is configured to select for each user a group of other users that are perceived by the user as peers. System 10 is configured to select the group based on one or more motivational criteria of the user and one or more social rankings of the user within one or more groups.

Social comparison (e.g., ranking within a social environment, group, etc.), competition, normalization, and prevention are four mechanisms that may be utilized for online coaching programs. These mechanisms may be beneficial because: (1) users may be anonymous (e.g., users in a group do not need to know each other, only that they are in the same group) and (2) direct communication between users may not be needed, thus eliminating the need for monitoring or screening messages being sent in the context of an online health coaching program. In some embodiments, system 10 may compare users to a group of users having similar profiles to determine a social ranking for each of the users in the group.

System 10 aggregates users into one or more groups. In some embodiments, system 10 determines, for each group, how well each user is doing compared to other users in the group. In some embodiments, system 10 provides a prediction of how well each user would do in comparison with other users in the group. In some embodiments, system 10 selects a first peer group for a user from the one or more groups such that the user's ranking within the first peer group corresponds to how the user is motivated from a ranking perspective. In some embodiments, system 10 changes a peer group selection for a user from the one or more groups such that the user's ranking within the newly selected peer group corresponds to how the user is motivated from a normalization perspective. In some embodiments, system 10 changes a peer group selection for a user from the one or more groups such that the user's ranking within the newly selected peer group corresponds to how the user is motivated from a preventative perspective. In some embodiments, system 10 includes one or more of a processor 12, electronic storage 14, external resources 16, a computing device 18, user device 22 or other components.

While FIG. 1 illustrates an example of a system, it will be appreciated that the methods described herein may be implemented in alternative systems. For example, in some systems, a separate computing device 18 may not be provided or the user interface 20 may be implemented in the user device 22 itself. Further, in some embodiments, the processor(s) 12 executing the instruction 24 (or subsets thereof) may be disposed in (or among) the user device 22, the computing device 18 (e.g., where the computing device 18 is a personal computer of the user), or a server (e.g., a virtual machine residing on server hardware in a cloud computing architecture) that provides a coaching or other data processing service.

Processor 12 is configured to provide information processing capabilities in system 10. As such, processor 12 may include one or more of a digital processor, an analog processor, a digital circuit designed to process information, an analog circuit designed to process information, a state machine, or other mechanisms for electronically processing information. Although processor 12 is shown in FIG. 1 as a single entity, this is for illustrative purposes only. In some embodiments, processor 12 may include a plurality of processing units. These processing units may be physically located within the same device (e.g., a server), or processor 12 may represent processing functionality of a plurality of devices operating in coordination (e.g., a server, computing device 18 associated with user 36, devices that are part of external resources 16, or other devices.)

As shown in FIG. 1, processor 12 is configured via machine-readable instructions 24 to execute one or more computer program components. As will be understood, in various embodiments, the instructions 24 may not literally reside on the processor (or may not all reside on the processor at a single time) but rather may be stored in a memory (e.g., the electronic storage 14) to be read and executed by the processor 12. The one or more computer program components may include one or more of a communications component 26, a user information component 28, a user aggregation component 30, a group selection component 32, a presentation component 34, or other components. Processor 12 may be configured to execute components 26, 28, 30, 32, or 34 by software; hardware; firmware; some combination of software, hardware, or firmware; or other mechanisms for configuring processing capabilities on processor 12.

It should be appreciated that although components 26, 28, 30, 32, and 34 are illustrated in FIG. 1 as being co-located within a single processing unit, in embodiments in which processor 12 includes multiple processing units, one or more of components 26, 28, 30, 32, or 34 may be located remotely from the other components. The description of the functionality provided by the different components 26, 28, 30, 32, or 34 described below is for illustrative purposes, and is not intended to be limiting, as any of components 26, 28, 30, 32, or 34 may provide more or less functionality than is described. For example, one or more of components 26, 28, 30, 32, or 34 may be eliminated, and some or all of its functionality may be provided by other components 26, 28, 30, 32, or 34. As another example, processor 12 may be configured to execute one or more additional components that may perform some or all of the functionality attributed below to one of components 26, 28, or 30.

Communications component 26 is configured to receive signals conveying health-related information associated with user 36. In some embodiments, the signals may be generated by one or more sensors including heart rate sensor, blood pressure sensor, respiration sensor, SpO2 oximetry (Oxygen saturation) sensor, stress level sensor, skin and core body temperature sensors, ECG sensor, weight scale, body fat percentage sensor, step count sensor, muscle quality sensor, GPS, accelerometer, gyroscope, or other sensors. Communications component 26 may receive the signals from the sensors. In some embodiments, the signals may be generated by user device 22 or other devices (e.g., user device 22 with such sensors or other devices). In some embodiments, communications component 26 may receive the signals from user device 22 via the sensors of user device 22.

User information component 28 is configured to determine health-related information associated with user 36 based on the received signals. In some embodiments, the determined health-related information includes a current health status (e.g., determined via a health score), an adherence to a program, an amount of physical activity, an amount of weight loss, a fitness level (e.g., estimated VO2 max) of user 36, contribution to motivating other users or other information. In some embodiments, user information component 28 is configured to determine a most optimal peer comparison strategy for user 36. In some embodiments, the most optimal peer comparison strategy is selected from one or more of a most motivational ranking, a most normalizing ranking, a most preventative ranking, or other strategies. In some embodiments, ranking user 36 according to the most motivational ranking may instill a desired health behavior in user 36. In some embodiments, ranking user 36 according to the most normalizing ranking may help to mediate negative consequences of not outperforming other users or underperforming towards personal aspirations. In some embodiments, ranking user 36 according to the most preventative ranking may be utilized for extremely competitive users who may be at a risk of over-straining physically or mentally. As such, a preventative ranking may place user 36 in peer groups with health aims that are opposite to risky behavior. For example, a pregnant and highly competitive woman would not be placed in a motivational exercise peer group; rather, she may be placed in a preventative relaxation peer group. In some embodiments, user information component 28 is configured to determine one or more motivational criteria for user 36. In some embodiments, the one or more motivational criteria include (i) being affiliated with a lower part of the first peer group (described below), wherein user 36 is motivated by social upward comparison; (ii) being affiliated with an upper part of the first peer group, wherein user 36 is motivated by social downward comparison; (iii) being almost highest ranked or highest ranked within the first peer group, wherein user 36 is motivated by competition; (iv) making more progress with respect to a social ranking (described below) within the first peer group than an average progress with respect to the social ranking within the first peer group, wherein user 36 is motivated by social upward comparison; or (v) making less progress with respect to the social ranking within the first peer group than an average progress with respect to the social ranking within the first peer group, wherein user 36 is motivated by social downward comparison. In some embodiments, the average progress is determined by averaging progress made by user 36 and other users of the first peer group with respect to the social ranking. In some embodiments, user information component 28 is configured to determine similarity criteria for user 36 and other users. In some embodiments, the similarity criteria includes at least one of having a similar gender, having a similar occupation, working at home, working part time/full time, being married/not, being pregnant/not, having children/not, having a similar weight, being in a similar region/location, having similar interests, having a similar education level, having a similar age, having similar activity levels, having similar fitness levels, having similar sleep scores, having similar stress levels, having a similar income range, or other criteria. In some embodiments, user information component 28 is configured to determine the one or more motivational criteria, similarity criteria, or other information based on one or more of a questionnaires, measured observed behavior, information provided by user 36's profile and other users' profile, similarity profiles with earlier users, or other resources. For example, characteristics including working at home, working part time/full time, and similar weight may be used for defining similarity between users and for clustering users in groups. In various embodiments, a user may manually specify their motivational criteria (e.g., by indicating that they are more motivated by maintaining a good rank or that they are more motivated by improving and initially bad rank).

In some embodiments, the system may automatically determine the motivational criteria for a user by applying, for example, one or more models trained using a machine learning algorithm on a population's data to extract motivational preferences from gathered behavior data. For example, the program may begin by trying multiple motivation criteria (and selecting matching social groups for reporting ranks as described herein) over a period of time and gauge the user's following performance in the program. The performance may then be fed into such a trained model (or analyzed according to some other algorithm) to identify which motivational criteria resulted the best performance. For example, the system may select a first group where the user is in the top 3 and a second group where the user is in the bottom 10%. After reporting the user's rank in the first group for a week, the system may log the user's compliance, rank, or other performance in the program. Then, the system may switch to reporting the user's rank in the second group and similarly log performance. If the performance improved in the second group, the system may then set the motivational criteria to match "social upward comparison." Such an model (e.g., one or more regression models or other classifiers) may be trained beforehand (or continually as new user data is gathered) using various algorithms (e.g. gradient descent) based on a database correlating user performance to a label indicating whether the current motivational criteria at that time was appropriate or even to a label indicating the motivational criteria ultimately deemed appropriate for that user.

User aggregation component 30 is configured to aggregate user 36 and other users into one or more groups. In some embodiments, user aggregation component 30 is configured to aggregate user 36 and the other users into the one or more groups based on one or more similarity criteria, as determined by the user information component 28. In some embodiments, user aggregation component 30 is configured to build a list of groups by taking a random subset of the similarity criteria resulting in >order $2^N$ number of groups (with N number of similarity criteria). The resulting number of groups is impacted by the type of variable per criterion (e.g. categorical or continuous) and number of variations (e.g., a response to being married results either in inclusion in group 'married' or "single," whereas a response to age may lead to inclusion in an exact age group or any possible grouping of different ages in one group). Additionally user specific weight factors may apply to each similarity criteria (e.g., it may be more important for a pregnant woman to be matched to other pregnant women than to women in general). In some embodiments, user aggregation component 30 is configured to determine a range or a threshold corresponding to the similarity criteria for including users in a group. For example, a 5-year threshold corresponding to age of users may be selected for including users in a group (e.g., other users either 5 years younger or older than user 36 may be placed in a group). In some embodiments, user aggregation component 30 is configured to determine one or more social rankings of the user within the one or more groups based on the health-related information. For example, user 36 may be compared with other users based on a number of steps walked during a day and ranked accordingly within the one or more groups. In some embodiments, user 36 and other users may be placed in one or more groups based on signals received from the one or more sensors and ranked based on one or more signals received from the one or more sensors. For example, users with similar muscle qualities are placed in a peer group. In this example, the users may be ranked based on activity levels (e.g., number of steps taken as determined by step-count sensor) or other criteria. In another example, users having a similar current health status (e.g., users with similar heart rates and blood pressures as determined by the heart rate sensor and blood pressure sensor respectively) may be placed in the same group and ranked according to one or more of activity levels (e.g., number of steps taken), muscle quality (as determined by muscle quality sensor), or other criteria. In this example, users having a higher health score may not be compared with users having a lower health score, as such a comparison may not motivate the users with higher health scores to maintain their high scores or may discourage the users having lower health scores from improving their health scores because achieving health scores similar to ones associated with users having higher health scores may not be realistic.

Group selection component 32 is configured to select a first peer group for the user from the one or more groups based on the one or more social rankings of the user and the one or more motivational criteria for the user. For example, user 36 may have a competitive mindset, thus being almost highest ranked or highest ranked (e.g., being ranked first in the first peer group) may be motivating to user 36. Furthermore, user 36 may be placed in a group based on the following characteristics: males with similar age (e.g., between 30 and 40 years old), with similar body mass index BMI (e.g., between 28 and 32), living in the same area (e.g., Amsterdam-region), and doing similar work, (e.g., office worker, full-time). In this example, if user 36 is not among the top in this group, comparing user 36 with other users may become demotivating; therefore, being placed in another group, in which user 36 is among the highest ranked may be more motivating for user 36. As such, user 36 may be placed in a first peer group including males between 30 and 40 of age, a BMI between 28 and 32, working full time and having commuting times longer than 1.5 hour per day. In some embodiments, group selection component 32 is configured to, responsive to the user achieving a social ranking corresponding to the one or more motivational criteria within the first peer group, maintain user 36 within the first peer group with the social ranking corresponding to the one or more motivational criteria for a predetermined amount of time. In some embodiments, group selection component 32 is configured to, subsequent to maintaining user 36 within the first peer group with the social ranking corresponding to the one or more motivational criteria of user 36 for the predetermined amount of time, place user 36 in a second peer group such that user 36 has not yet achieved the social ranking corresponding to the one or more motivational criteria within the second peer group. In some embodiments, the second peer group has at least one different individual member than the first peer group. For example, user 36 who may be motivated by being almost highest ranked or highest ranked in a group, responsive to being ranked first in the first peer group, may remain first ranked in the first peer group for a predetermined amount of time. In this example, since user 36 is motivated by ranking up from second place to first place within a group, user 36 may be reassigned to a second peer group in which user 36 has not yet achieved the highest ranking subsequent to remaining first ranked in the first peer group for the predetermined amount of time. In some embodiments, group selection component 30 is configured to determine a normalized social ranking of user 36 within the first peer group such that a stress associated with user 36 or other users is reduced or eliminated. For example, user 36 may be participating in a weight loss program. Furthermore, user 36 may notice an under-performance with respect to his/her personally set weight targets (e.g., user 36 may not have lost as much weight as user 36 desired). In this example, group selection component 32 may rank user 36 and other users within the first peer group based on a normalized progress made (e.g., amount of progress made toward set target) by user 36 and the other user. The normalized social ranking may reveal that other users may also be struggling in achieving their respective goals and may help to mediate negative consequences of not outperforming others or underperforming towards personal aspirations. In some embodiments, system 10 may place user 36 in the second peer group such that user 36's ranking within the second peer group corresponds to how user 36 is motivated from a normalization perspective. In some embodiments, system 10 may place user 36 in the second peer group such that user 36's ranking within the second peer group corresponds to how user 36 is motivated from a preventative perspective. By way of a non-limiting example, Table 1 illustrates motivational criteria that may apply to each of the peer comparison strategies. In this example, responsive to an indication that normalization is required, system 10 may implement a shift the peer comparison strategy from a core or preferred user strategy.

TABLE 1

| | Motivational | Normalizing | Preventative |
|---|---|---|---|
| Social upward comparison: being affiliated with a lower part of group | X | | |
| Social upward comparison: making more progress than average of group | X | X | X |
| Social downward comparison: being affiliated with an upper part of group | X | X | X |
| Social downward comparison: making less progress than average of group | X | X | |
| Competition: being ranked almost #1 | X | | |

Presentation component 34 is configured to effectuate presentation of the user's social ranking within the first peer group. In some embodiments, presentation component 34 is configured to provide progress updates for user 36 and other users within the first peer group. As such user 36 may be motivated by peer pressure to match his/her progress to progress made by the other users within the first peer group or exceed progress made by the other users within the first peer group. In some embodiments, presentation component is configured to effectuate presentation of user 36's normalized social ranking within the first peer group. In some embodiments, presentation component 34 may effectuate presentation of an absolute ranking position of user 36 within the first peer group (e.g., being number 4) and a relative position of user 36 within the first peer group (e.g., out of 23). The absolute ranking position of user 36 may instill the desired health behavior in user 36 that is motivated by competition, whereas the relative position of user 36 may help to mediate negative consequences of not outperforming others or underperforming towards personal aspirations. In some embodiments, ranking of user 36 and the other users may be presented in numbers, visualizations, graphs, charts, tables, 3-dimensional images, augmented reality views, or formats.

As shown in FIG. 1, system 10 may include the user device 22. In some embodiments, user device 22 includes one or more sensors configured to generate signals conveying the health-related information associated with user 36. The one or more sensors may include heart rate sensor, blood pressure sensor, respiration sensor, SpO2 oximetry (Oxygen saturation) sensor, stress level sensor, skin and core body temperature sensors, ECG sensor, weight scale, body fat percentage sensor, step count sensor, muscle quality sensor, GPS, accelerometer, gyroscope, or other sensors. In some embodiments, user device 22 is configured to receive health-related information associated with the other users of the first peer group over a network in communication with the processor 12 (e.g., user information component 28).

In some embodiments, user device 22 is configured to determine an auxiliary social ranking of the user within the first peer group based on the health-related information associated with the user and the health-related information associated with the other users of the first peer group. To ensure secure privacy and security of health-related information, the health-related information may be stored on user device 22 in any aggregated and anonymized way or only relative rankings based on health-related information may be stored on user device 22. In some embodiments, user device 22 is configured to determine, based on further signals generated by the one or more sensors, additional health-related information associated with user 36. In some embodiments, user device 22 is configured to update the auxiliary social ranking of user 36 based on the additional health-related information such that user 36's updated auxiliary social ranking is different than user 36's social ranking within the first peer group at a given time. In some embodiments, user device 22 is configured to effectuate presentation of user 36's updated auxiliary social ranking at user device 22. For example user device 22 may determine a number of steps taken by user 36 in a particular day. Furthermore, user device 22 may have previously downloaded information over a network with respect to a performance of all of the other users within the first peer group. In this example, user device 22 may determine user 36's ranking (e.g., auxiliary ranking) in real-time based on the previously downloaded information. In some embodiments, user device 22 is configured to provide a real-time auxiliary ranking of user 36 when user device 22 is offline (e.g. not connected to the Internet or unable to receive the health-related information associated with the other users of the first peer group due to a slow network connection). In this way, for instance, user 36 need not wait for user device 22 to come online before being provided with his/her real-time auxiliary ranking. In some embodiments, user device 22 is configured to provide the real-time auxiliary ranking of user 36 based on the additional health-related information and previously received health-related information associated with the other users of the first peer group. As an example, user device 22 stores previously received health-related information associated with the other users of the first peer group, and uses the stored previously received health-related information (associated with the other users of the first peer group) in conjunction with additional health-related information (associated with the user) obtained in real-time at user device 22 to determine the real-time auxiliary ranking of user 36 without user device 22 being required to be connected to the Internet. Specifically, for instance, the real-time auxiliary ranking of user 36 may be an approximation of the user's actual ranking based on the user's real-time health-related information (e.g., derived from sensors of user device 22) and the other user's non-real-time health-related information (e.g., possibly outdated health-related information). As such, the approximation may be determined by user device 22 without needing to obtain the real-time health-related information associated with the other users of the first peer group (e.g., and, thus, without needing to connect to the Internet to do so). In some embodiments, user device 22 may update user 36's auxiliary ranking when user device 22 comes online (e.g. connected to the network) based on newly received health-related information associated with the other users of the first peer group. In some embodiments, user device 22 may include algorithms to predict ranking changes of other users based on latest received rankings and health-related information of the other users and historical change patterns per user. In some embodiments, processor 12 may provide pre-processed prediction curves of users' behaviors to device 22 such that a close-to-real-time approximation of most likely auxiliary ranking are presented in order to minimize the adaptation needed after reconnecting user device 22 to the internet.

Electronic storage 14 includes electronic storage media that electronically stores information. The electronic storage media of electronic storage 14 may include one or both of system storage that is provided integrally (i.e., substantially non-removable) with system 10 or removable storage that is removably connectable to system 10 via, for example, a port (e.g., a USB port, a firewire port, etc.) or a drive (e.g., a disk drive, etc.). Electronic storage 14 may be (in whole or in part) a separate component within system 10, or electronic storage 14 may be provided (in whole or in part) integrally with one or more other components of system 10 (e.g., computing device 18, processor 12, etc.). In some embodiments, electronic storage 14 may be located in a server together with processor 12, in a server that is part of external resources 16, in computing device 18 associated with user 36, or other users, or in other locations. Electronic storage 14 may include one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), or other electronically readable storage media. As used herein, the term "non-transitory" when used to describe machine/computer-readable media will be understood to include both volatile and non-volatile memories, but to exclude transitory signals. Electronic storage 14 may store software algorithms, information determined by processor 12, information received via computing device 18 or other external computing systems, information received from external resources 16, or other information that enables system 10 to function as described herein. By way of a non-limiting example, electronic storage 14 may store the threshold corresponding to the similarity criteria, health-related information associated with user 36 and other users or other information.

External resources 16 include sources of information (e.g., databases, websites, etc.), external entities participating with system 10 (e.g., one or more sensors configured to generate signals conveying the health-related information), one or more servers outside of system 10, a network (e.g., the internet), electronic storage, equipment related to Wi-Fi technology, equipment related to Bluetooth® technology, data entry devices, computing devices associated with individual users, or other resources. In some implementations, some or all of the functionality attributed herein to external resources 16 may be provided by resources included in system 10. External resources 16 may be configured to communicate with processor 12, computing device 18, electronic storage 14, or other components of system 10 via wired or wireless connections, via a network (e.g., a local area network or the internet), via cellular technology, via Wi-Fi technology, or via other resources.

Computing device 18 is configured to provide an interface between user 36, or other users and system 10. Computing device 18 is configured to provide information to or receive information from the user 36, or other users. For example, computing device 18 is configured to present a user interface 20 to user 36 to facilitate presentation of user 36's social ranking to user 36. In some embodiments, user interface 20 includes a plurality of separate interfaces associated with computing device 18, processor(s) 12 or other components of system 10.

In some embodiments, computing device 18 is configured to provide user interface 20, processing capabilities, databases, or electronic storage to system 10. As such, computing device 18 may include processor(s) 12, electronic storage 14, external resources 16, or other components of system 10. In some embodiments, computing device 18 is connected to a network (e.g., the internet). In some embodiments, computing device 18 does not include processor(s) 12, electronic storage 14, external resources 16, or other components of system 10, but instead communicate with these components via the network. The connection to the network may be wireless or wired. For example, processor(s) 12 may be located in a remote server and may wirelessly cause display of user interface 20 to user 36 on computing device 18. In some embodiments, computing device 18 is a laptop, a personal computer, a smartphone, a tablet computer, a smart watch, an activity tracker, or other computing devices. Examples of user input devices suitable for inclusion in computing device 18 include a touch screen, a keypad, touch sensitive or physical buttons, switches, a keyboard, knobs, levers, a display, speakers, a microphone, an indicator light, an audible alarm, a printer, or other interface devices. The present disclosure also contemplates that computing device 18 includes a removable storage interface. In this example, information may be loaded into computing device 18 from removable storage (e.g., a smart card, a flash drive, a removable disk) that enables the user 36, or other users to customize the implementation of computing device 18. Other exemplary input devices and techniques adapted for use with computing device 18 include, but are not limited to, an RS-232 port, RF link, an IR link, a modem (telephone, cable, etc.) or other devices. In some embodiments, user 36 or other users provide responses to questionnaires or other information via one or more user input devices.

Figure 2:
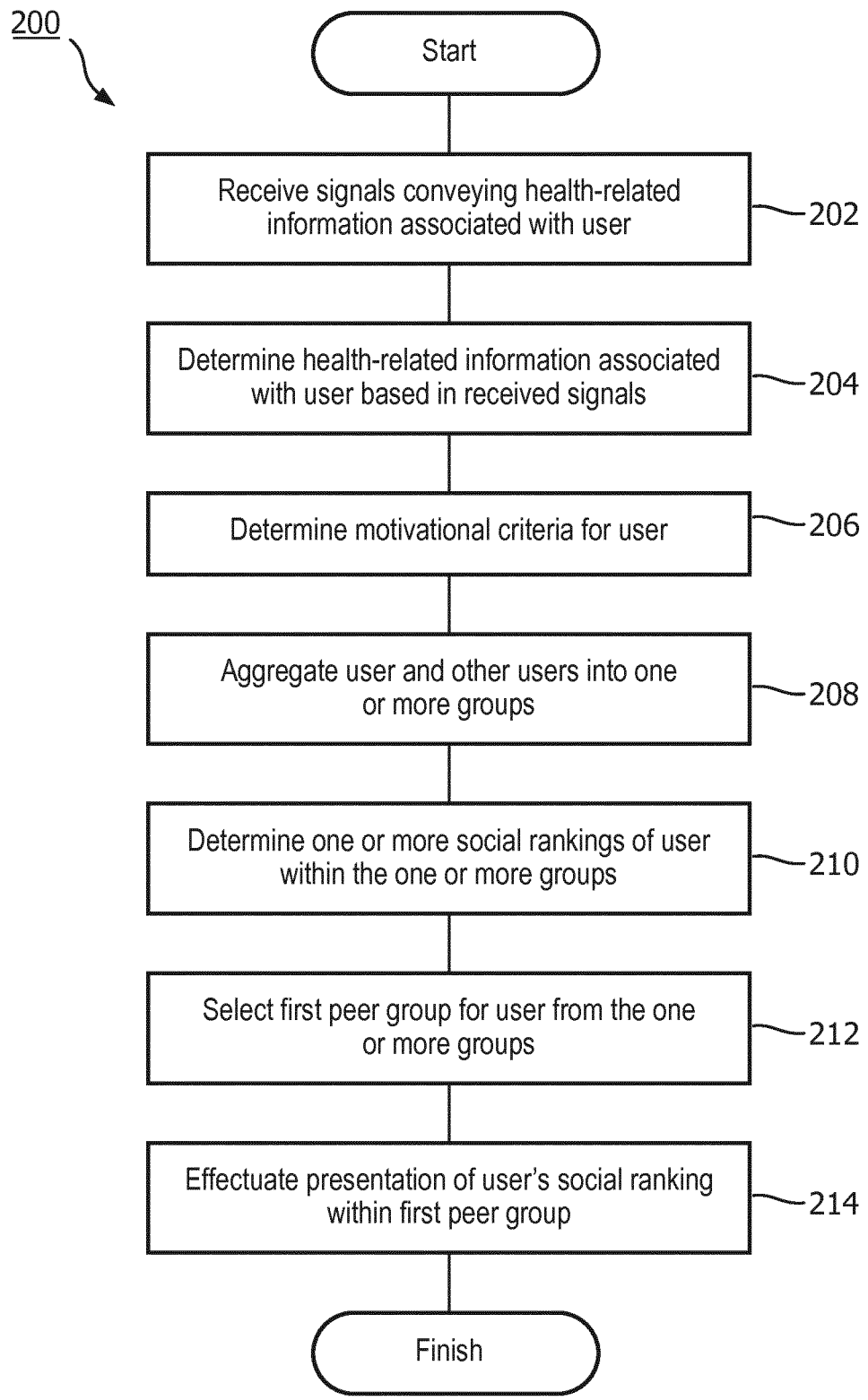
FIG. 2 illustrates a method for facilitating social ranking and grouping via received signals conveying health-related information according to one or more embodiments.

FIG. 2 illustrates a method 200 for facilitating social ranking and grouping via received signals conveying health-related information with a system. The system includes one or more processors or other components. The one or more processors are configured by machine readable instructions to execute computer program components. The computer program components include a communications component, a user information component, a user aggregation component, a group selection component, a presentation component, or other components. The operations of method 200 presented below are intended to be illustrative. In some embodiments, method 200 may be accomplished with one or more additional operations not described, or without one or more of the operations discussed. Additionally, the order in which the operations of method 200 are illustrated in FIG. 2 and described below is not intended to be limiting.

In some embodiments, method 200 may be implemented in one or more processing devices (e.g., a digital processor, an analog processor, a digital circuit designed to process information, an analog circuit designed to process information, a state machine, or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, or software to be specifically designed for execution of one or more of the operations of method 200.

At an operation 202, signals conveying health-related information associated with a user are received. In some embodiments, the signals may include information related to physiological parameters, fitness parameters, or other parameters of the user. In some embodiments, the signals may be generated by one or more sensors including heart rate sensor, blood pressure sensor, respiration sensor, SpO2 oximetry (Oxygen saturation) sensor, stress level sensor, skin and core body temperature sensors, ECG sensor, weight scale, body fat percentage sensor, step count sensor, muscle quality sensor, GPS, accelerometer, gyroscope, or other sensors. In some embodiments, operation 202 is performed by a processor component the same as or similar to communications component 26 (shown in FIG. 1 and described herein).

At an operation 204, health-related information associated with the user is determined based on the received signals. In some embodiments, the determined health-related information includes a current health status, an adherence to a program, an amount of physical activity, an amount of weight loss or weight loss percentage since start of the program, a fitness level of the user, or other information. In some embodiments, operation 204 is performed by a processor component the same as or similar to user information component 28 (shown in FIG. 1 and described herein).

At an operation 206, one or more motivational criteria for the user are determined. In some embodiments, the one or more motivational criteria include being affiliated with a lower part of a first peer group (discussed at operation 212 below), wherein the user is motivated by social upward comparison; being affiliated with an upper part of the first peer group, wherein the user is motivated by social downward comparison; being almost highest ranked or highest ranked within the first peer group, wherein the user is motivated by competition; making more progress with respect to the social ranking within the first peer group than an average progress with respect to the social ranking within the first peer group, wherein the user is motivated by social upward comparison; or making less progress with respect to the social ranking within the first peer group than an average progress with respect to the social ranking within the first peer group, wherein the user is motivated by social downward comparison. In some embodiments, the average progress is determined by averaging progress made by each of the individual members of the first peer group with respect to the social ranking. In some embodiments, operation 206 is performed by a processor component the same as or similar to user information component 28 (shown in FIG. 1 and described herein).

At an operation 208, the user and other users are aggregated into one or more (e.g., in some embodiments, at least two) groups. In some embodiments, the user and the other users are aggregated into the one or more groups based on one or more similarity criteria, wherein the one or more similarity criteria is determined based on information provided on the user's profile and the other users' profiles. In some embodiments, the similarity criteria includes one or more of a gender, a location, an occupation, a marital status, an employment status, an education level, an age, an activity level, a fitness level, an interest of the user and each of the other users, or other information. As such, various embodiments generate a set of candidate groupings for selection (later, according to the motivational criteria) that rather than being arbitrary, have some relevance to the user because the user is in at least one way similar to the other users in the group. In some embodiments, operation 208 is performed by a processor component the same as or similar to user aggregation component 30 (shown in FIG. 1 and described herein).

At an operation 210, one or more social rankings of the user within the one or more groups are determined based on the health-related information. In some embodiments, operation 210 is performed by a processor component the same as or similar user aggregation component 30 (shown in FIG. 1 and described herein).

At an operation 212, a first peer group is selected for the user from the one or more groups based on the one or more social rankings of the user and the one or more motivational criteria for the user. In some embodiments, the social ranking of the user within the selected first peer group corresponds best with his/her one or more motivational criteria. In some embodiments, responsive to the user achieving a social ranking corresponding to the one or more motivational criteria within the first peer group, the user is maintained within the first peer group with the social ranking corresponding to the one or more motivational criteria for a predetermined amount of time. In some embodiments, subsequent to maintaining the user within the first peer group with the social ranking corresponding to the one or more motivational criteria for the predetermined amount of time, the user is placed in a second peer group such that the user has not yet achieved the social ranking corresponding to the one or more motivational criteria within the second peer group. In some embodiments, the second peer group has at least one different individual member than the first peer group. In some embodiments, operation 212 is performed by a processor component the same as or similar to group selection component 32 (shown in FIG. 1 and described herein).

At an operation 214, the user's social ranking within the first peer group is presented. Such presentation may be made via the computing device (e.g., PC, mobile phone, or tablet) using push notifications, email, SMS messages, etc. or may be made via the user device (e.g., a wearable wrist-watch or patch device). In some embodiments, the ranking may indicate the group to which the user belongs (e.g., "You are ranked $3^{rd}$ in your company. Congratulations!" or "Among 30-something males in Boston, you are in the bottom 10%") In some embodiments, operation 214 may further include: receiving, with a user device, health-related information associated with the other users of the first peer group over a network in communication with the one or more processors; determining, with the user device, an auxiliary social ranking of the user within the first peer group based on the health-related information associated with the user and the health-related information associated with the other users of the first peer group; determining, with the user device, additional health-related information associated with the user based on further signals generated by the user device; updating, with the user device, the auxiliary social ranking of the user based on the additional health-related information such that the user's updated auxiliary social ranking is different than the user's social ranking within the first peer group at a given time; and effectuating, with the user device, presentation of the user's updated auxiliary social ranking at the user device. In some embodiments, operation 210 is performed by a processor component the same as or similar to presentation component 34 (shown in FIG. 1 and described herein).

It will be apparent that the method 200 is only one possible example of a method for implementing the concepts described herein and that alternative methods may be devised consistent with these principles. For example, in some embodiments, the method 200 is split between two independent methods. A first method may include steps 206, 208, 210, 212, and may run periodically (e.g., daily, weekly, monthly) to select the appropriate peer group for the user. The second method may include steps 202, 204, 214 and may run more frequently (e.g., continually, hourly, daily) to gather information from the user, gauge performance against the currently selected peer group, and present the ranking as (and potentially along with other) motivation. In some such embodiments, the two methods may be performed by two different devices, with one device informing the other as to the selected peer group.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

It should be apparent from the foregoing description that various example embodiments of the invention may be implemented in hardware or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention.

What is claimed is:

1. A system configured to facilitate social ranking and grouping via received signals conveying health-related information, the system comprising one or more processors configured by machine-readable instructions to:
   receive signals conveying health-related information associated with a user;
   determine health-related information associated with the user based on the received signals;
   determine one or more motivational criteria for the user;
   aggregate the user and other users into one or more groups;
   determine one or more social rankings of the user within the one or more groups based on the health-related information;
   select a first peer group for the user from the one or more groups based on the one or more social rankings of the user and the one or more motivational criteria for the user; and
   effectuate presentation of the user's social ranking within the first peer group,
   and further comprising a user device, the user device including one or more sensors configured to generate signals conveying the health-related information associated with the user, wherein the user device is configured to:
   receive health-related information associated with the other users of the first peer group over a network in communication with the one or more processors;
   and wherein, when offline, the user device is further configured to:
   determine an auxiliary social ranking of the user within the first peer group based on the health-related information associated with the user and the health-related information associated with the other users of the first peer group;
   determine, based on further signals generated by the one or more sensors, additional health-related information associated with the user;
   update the auxiliary social ranking of the user based on the additional health-related information such that the user's updated auxiliary social ranking is different than the user's social ranking within the first peer group at a given time; and
   effectuate presentation of the user's updated auxiliary social ranking at the user device.

2. The system of claim 1, wherein the one or more motivational criteria are determined based on at least one of a most motivational ranking, a most normalizing ranking, and a most preventative ranking, and wherein the one or more motivational criteria comprise:

being affiliated with a lower part of the first peer group, wherein the user is motivated by social upward comparison;

being affiliated with an upper part of the first peer group, wherein the user is motivated by social downward comparison;

being almost highest ranked within the first peer group, wherein the user is motivated by competition;

making more progress with respect to the social ranking within the first peer group than an average progress with respect to the social ranking within the first peer group, wherein the user is motivated by social upward comparison; or making less progress with respect to the social ranking within the first peer group than an average progress with respect to the social ranking within the first peer group, wherein the user is motivated by social downward comparison, and wherein the average progress is determined by averaging progress made by the user and each of the other users of the first peer group with respect to the social ranking.

3. The system of claim 1, wherein the determined health-related information includes at least one of a current health status, an adherence to a program, an amount of physical activity, an amount of weight loss, and a fitness level of the user.

4. The system of claim 1, wherein the one or more processors are further configured to:

responsive to the user achieving a social ranking corresponding to the one or more motivational criteria within the first peer group, maintain the user within the first peer group with the social ranking corresponding to the one or more motivational criteria for a predetermined amount of time; and subsequent to maintaining the user within the first peer group with the social ranking corresponding to the one or more motivational criteria for the predetermined amount of time, place the user in a second peer group such that the user has not yet achieved the social ranking corresponding to the one or more motivational criteria within the second peer group, the second peer group having at least one different individual member than the first peer group.

5. The system of claim 1, wherein the one or more processors are configured to aggregate the user and the other users into the one or more groups based on one or more similarity criteria, wherein the one or more similarity criteria is determined based on information provided on the user's profile and the other users' profiles.

6. The system of claim 5, wherein the similarity criteria comprises at least one of a gender, a location, an occupation, a marital status, an employment status, an education level, an age, an activity level, a fitness level, and an interest of the user and each of the other users.

7. A method for facilitating social ranking and grouping via received signals conveying health-related information, the method being implemented by a computer system including one or more processors configured by machine-readable instructions, the method comprising:

receiving, with the one or more processors, signals conveying health-related information associated with a user;

determining, with the one or more processors, health-related information associated with the user based on the received signals;

determining, with the one or more processors, one or more motivational criteria for the user;

aggregating, with the one or more processors, the user and other users into one or more groups;

determining, with the one or more processors, one or more social rankings of the user within the one or more groups based on the health-related information;

selecting, with the one or more processors, a first peer group for the user from the one or more groups based on the one or more social rankings of the user and the one or more motivational criteria for the user; and effectuating, with the one or more processors, presentation of the user's social ranking within the first peer group, wherein the system further comprises a user device, the user device including one or more sensors configured to generate signals conveying the health-related information associated with the user, wherein the method further comprises:

receiving, with the user device, health-related information associated with the other users of the first peer group over a network in communication with the one or more processors, and wherein, when the user device is offline, the method further comprises:

determining, with the user device, an auxiliary social ranking of the user within the first peer group based on the health-related information associated with the user and the health-related information associated with the other users of the first peer group;

determining, with the user device, additional health-related information associated with the user based on further signals generated by the one or more sensors;

updating, with the user device, the auxiliary social ranking of the user based on the additional health-related information such that the user's updated auxiliary social ranking is different than the user's social ranking within the first peer group at a given time; and effectuating, with the user device, presentation of the user's updated auxiliary social ranking at the user device.

8. The method of claim 7, wherein the one or more motivational criteria are determined based on at least one of a most motivational ranking, a most normalizing ranking, and a most preventative ranking, and wherein the one or more motivational criteria comprise:

being affiliated with a lower part of the first peer group, wherein the user is motivated by social upward comparison;

being affiliated with an upper part of the first peer group, wherein the user is motivated by social downward comparison;

being almost highest ranked within the first peer group, wherein the user is motivated by competition;

making more progress with respect to the social ranking within the first peer group than an average progress with respect to the social ranking within the first peer group, wherein the user is motivated by social upward comparison; or making less progress with respect to the social ranking within the first peer group than an average progress with respect to the social ranking within the first peer group, wherein the user is motivated by social downward comparison, and wherein the average progress is determined by averaging progress made by the user and each of the other users of the first peer group with respect to the social ranking.

9. The method of claim 7, wherein the determined health-related information includes at least one of a current health status, an adherence to a program, an amount of physical activity, an amount of weight loss, and a fitness level of the user.

10. The method of claim 7, further comprising:

responsive to the user achieving a social ranking corresponding to the one or more motivational criteria within the first peer group, maintaining the user within the first peer group with the social ranking corresponding to the one or more motivational criteria for a predetermined amount of time; and subsequent to maintaining the user within the first peer group with the social ranking corresponding to the one or more motivational criteria for the predetermined amount of time, placing the user in a second peer group such that the user has not yet achieved the social ranking corresponding to the one or more motivational criteria within the second peer group, the second peer group having at least one different individual member than the first peer group.

11. The method of claim 7, wherein the user and the other users are aggregated into the one or more groups based on one or more similarity criteria, wherein the one or more similarity criteria is determined based on information provided on the user's profile and the other users' profiles.

12. The method of claim 11, wherein the similarity criteria comprises at least one of a gender, a location, an occupation, a marital status, an employment status, an education level, an age, an activity level, a fitness level, and an interest of the user and each of the other users.

13. A non-transitory machine-readable storage medium comprising instructions for execution by a processor for facilitating social ranking and grouping via received signals conveying health-related information, the A non-transitory machine-readable storage medium comprising:

instructions for determining one or more motivational criteria for the user;

instructions for aggregating the user and other users into two or more groups;

instructions for determining one or more social rankings of the user within the two or more groups based on health-related information of the user; and instructions for selecting a first peer group for the user from the one or more groups based on the one or more social rankings of the user and the one or more motivational criteria for the user; and instructions for receiving, with a user device including one or more sensors configured to generate signals conveying the health-related information associated with the user, health-related information associated with the other users of the first peer group over a network in communication with the one or more processors, and further comprising instructions for, when the user device is offline:

determining an auxiliary social ranking of the user within the first peer group based on the health-related information associated with the user and the health-related information associated with the other users of the first peer group;

determining, based on further signals generated by one or more sensors, additional health-related information associated with the user;

updating the auxiliary social ranking of the user based on the additional health-related information such that the user's updated auxiliary social ranking is different than the user's social ranking within the first peer group at a given time; and effectuating presentation of the user's updated auxiliary social ranking at the user device.

14. The non-transitory machine-readable storage medium of claim 13, wherein the one or more motivational criteria are determined based on at least one of a most motivational ranking, a most normalizing ranking, and a most preventative ranking, and wherein the one or more motivational criteria comprise:

being affiliated with a lower part of the first peer group, wherein the user is motivated by social upward comparison;

being affiliated with an upper part of the first peer group, wherein the user is motivated by social downward comparison;

being almost highest ranked within the first peer group, wherein the user is motivated by competition;

making more progress with respect to the social ranking within the first peer group than an average progress with respect to the social ranking within the first peer group, wherein the user is motivated by social upward comparison; or making less progress with respect to the social ranking within the first peer group than an average progress with respect to the social ranking within the first peer group, wherein the user is motivated by social downward comparison, and wherein the average progress is determined by averaging progress made by the user and each of the other users of the first peer group with respect to the social ranking.

15. The non-transitory machine-readable storage medium of claim 13, wherein the health-related information includes at least one of a current health status, an adherence to a program, an amount of physical activity, an amount of weight loss, and a fitness level of the user.

* * * * *